(12) United States Patent
Kuo

(10) Patent No.: US 7,300,001 B2
(45) Date of Patent: Nov. 27, 2007

(54) PUMP-DISPENSING ATOMIZER

(76) Inventor: Roy Kuo, No. 288, Chin-Chow St., Taipei (TW)

( * ) Notice: Subject to any disclaimer, the term of this patent is extended or adjusted under 35 U.S.C. 154(b) by 232 days.

(21) Appl. No.: 11/217,309

(22) Filed: Sep. 2, 2005

(65) Prior Publication Data
US 2007/0051831 A1 Mar. 8, 2007

(51) Int. Cl.
*B05B 9/043* (2006.01)
(52) U.S. Cl. .................. 239/333; 239/337; 239/427; 239/463; 239/469; 239/487; 239/488; 239/499; 239/518
(58) Field of Classification Search ......... 222/321.7, 222/321.9, 383.1; 239/333, 337, 338, 427, 239/463, 469, 487, 488, 491, 499, 518, 592, 239/593
See application file for complete search history.

(56) References Cited

U.S. PATENT DOCUMENTS

| | | | | |
|---|---|---|---|---|
| 3,239,151 A | * | 3/1966 | Jokelson | 239/333 |
| 3,471,092 A | * | 10/1969 | Hickey | 239/579 |
| 4,187,985 A | * | 2/1980 | Goth | 239/337 |
| 5,622,318 A | * | 4/1997 | Bougamont et al. | 239/490 |
| 5,711,488 A | * | 1/1998 | Lund | 239/333 |
| 5,934,518 A | * | 8/1999 | Stern et al. | 222/402.1 |
| 6,508,810 B1 | * | 1/2003 | Ouchi et al. | 606/1 |
| 6,533,196 B1 | * | 3/2003 | Ouin et al. | 239/476 |
| 6,776,312 B2 | * | 8/2004 | Masuzzo et al. | 222/321.7 |
| 2003/0230641 A1 | * | 12/2003 | Foster et al. | 239/333 |
| 2005/0023376 A1 | * | 2/2005 | Anderson | 239/432 |

* cited by examiner

*Primary Examiner*—Kevin Shaver
*Assistant Examiner*—Jason Boeckmann

(57) ABSTRACT

A pump-dispensing atomizer includes a dispensing pump with a closure to engage with a container. The dispensing pump includes a pressing button with a booster chamber formed inside, a nozzle with one end extending from the pressing button and a probe formed with at least one section. An interior of the nozzle is formed with a guide chamber, and one end of the guide chamber is connected to the booster chamber. The guide chamber has at least one expanding sub-chamber. After the probe is disposed in the guide chamber, a boosting channel is formed between the expanding sub-chamber and the stepped section. Moreover, the pressure accumulator is mounted on the other end of the nozzle, which is formed with a spraying opening communicated to outer environment. As such, the pressure of liquid flowing in the nozzle will be increased effectively so that liquid is sprayed out with a higher pressure to increase the spraying speed of the liquid.

6 Claims, 5 Drawing Sheets

A-A

B-B

C-C

PUMP-DISPENSING ATOMIZER

CROSS-REFERENCE TO RELATED APPLICATIONS

This application is related to Applicant's U.S. patent application Ser. No. 10/795,833, filed Mar. 9, 2004, now U.S. Pat. No. 6,851,625, the disclosures of which are incorporated herein by reference.

BACKGROUND OF THE INVENTION

The present invention relates to a pump-dispensing atomizer, and in particular to an atomizer of reciprocating pump type that can increase liquid speed in the spout so that when the liquid is sprayed out by pressing on the pump, the liquid is pressurized to have a higher spraying speed.

Typically, trigger-action atomizers are operated by triggering a handle to produce a fine mist or an atomized spray, and pump-dispensing atomizers by pressing on a pump. The former are generally used for spraying water or cleaner; the latter are used for spraying throat medicine, perfume or hair aerosol.

U.S. Pat. No. 6,851,625 disclosed a trigger-action atomizer includes a triggering handle to actuate spraying liquid with high speeds. A booster chamber and a plurality of boosting channels are provided to pressurize the liquid to spray out in finer liquid particle sizes resulting in a referred atomization effect.

However, for an atomizer of reciprocating pump type, there is still no such design to sufficiently atomize liquid. Therefore, the spraying speed is too low for current pump-dispensing atomizer so that the atomizing effect is not preferred and effective spraying coverage will reduce for use in spraying throat medicine, perfume or hair aerosol.

BRIEF SUMMARY OF THE INVENTION

Due to the pump actuation is different from the handle trigger, the present invention is to redesign a pump-dispensing atomizer with high spraying speeds.

Accordingly, a pump-dispensing atomizer of the present invention includes a dispensing pump with a closure to engage with a container. The dispensing pump includes a pressing button with a booster chamber formed inside, a nozzle with one end extending from the pressing button and a probe formed with at least one section. An interior of the nozzle is formed with a guide chamber, and one end of the guide chamber is connected to the booster chamber. The guide chamber has at least one expanding sub-chamber. After the probe is disposed in the guide chamber, a boosting channel is formed between the expanding sub-chamber and the stepped section. Moreover, the pressure accumulator is mounted on the other end of the nozzle, which is formed with a spraying opening communicated to outer environment.

The various objects and advantages of the present invention will be more readily understood from the following detailed description when read in conjunction with the appended drawing.

DETAILED DESCRIPTION OF THE INVENTION

In order that those skilled in the art can further understand the present invention, a description will be described in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
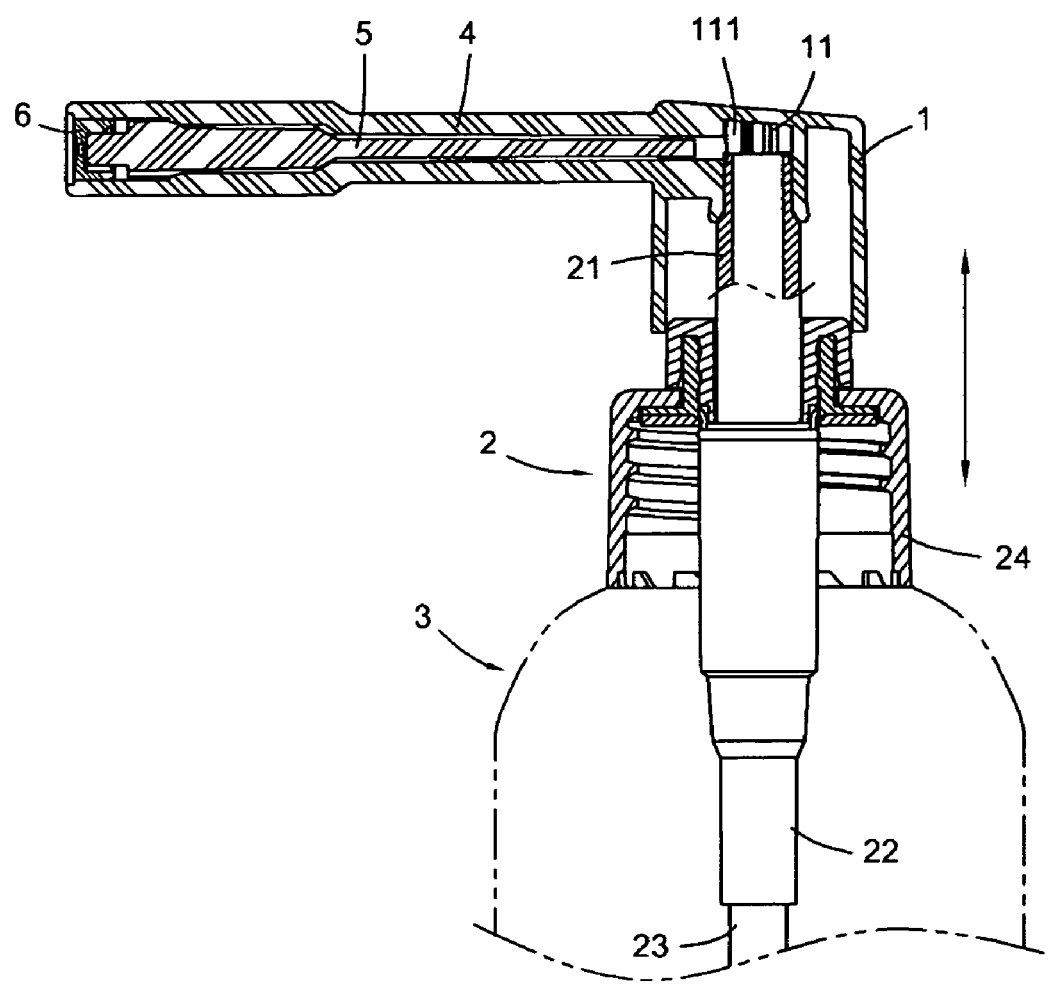
FIG. 1 is a cross sectional view of a pump-dispensing atomizer to show a dispensing pump with a pressing button mounted on a container.

Referring to FIG. 1, an atomizer of reciprocating pump type according to the present invention includes a dispensing pump 2 mounted on a container 3. The dispensing pump 2 includes a pressing button 1.

Figure 2:
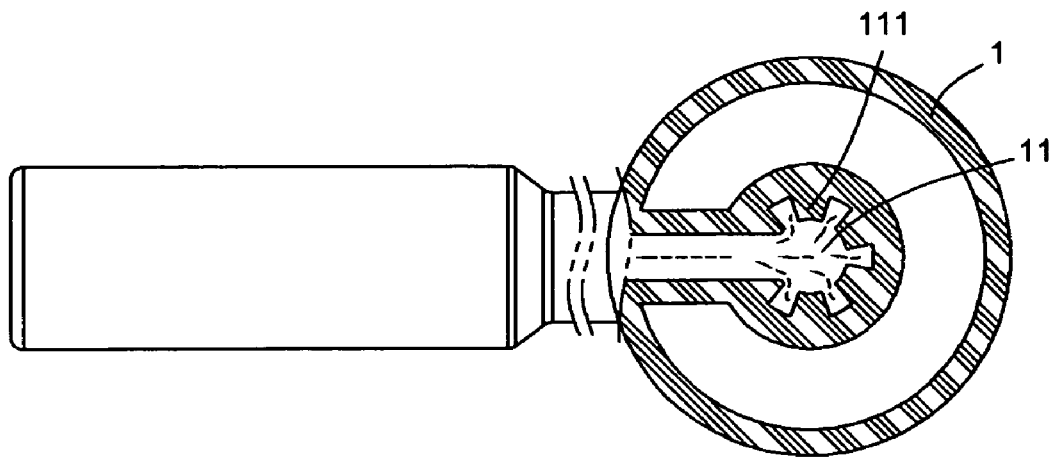
FIG. 2 is a cross sectional view of the button from top to show plural booster posts formed in a booster chamber.
Figure 3:
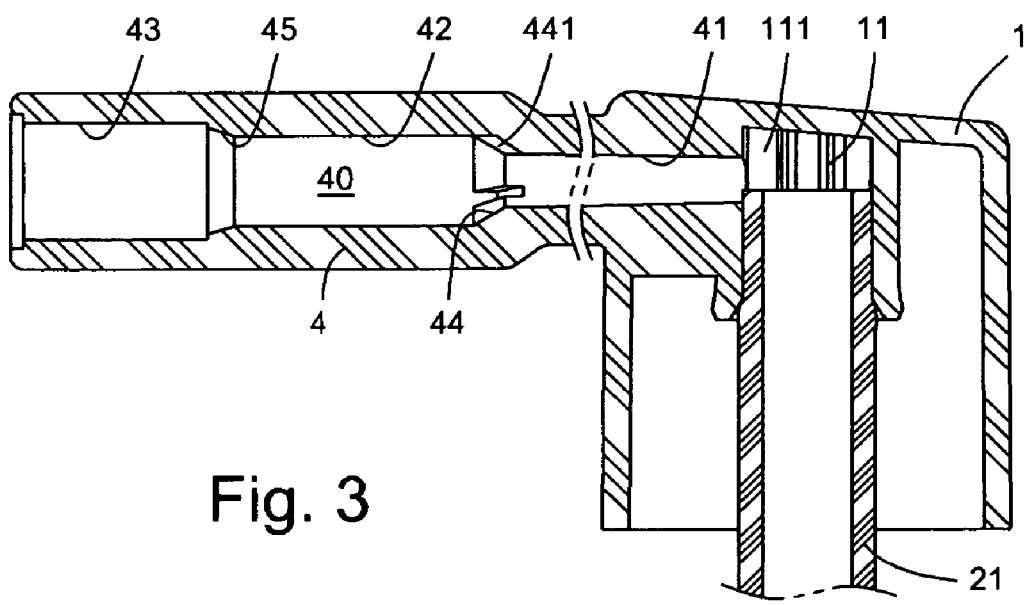
FIG. 3 is a cross sectional view of the button to show a guide chamber of a nozzle extending from the button.
Figure 4:
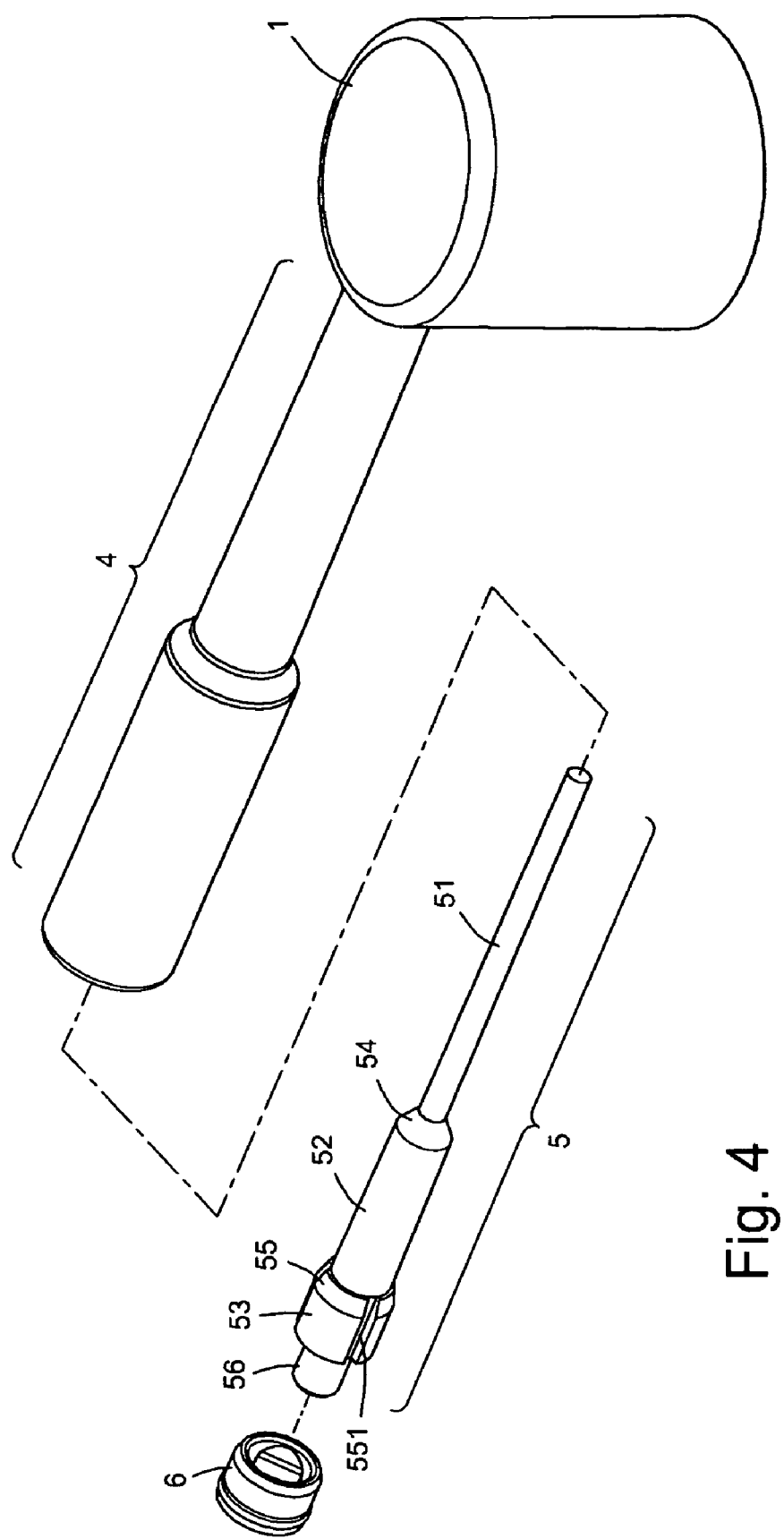
FIG. 4 is a perspective exploded view of the button to show a probe inserted in the guide chamber and a pressure accumulator mounted on the open end of the nozzle.

Together referring to FIGS. 2 and 3, the pressing button 1 has a stand type booster chamber 11 formed therein. A plurality of booster posts 111 are formed on top of the inner wall of the booster chamber 11. A nozzle 4 is extended from a side of the pressing button 1, as shown in FIG. 4.

As shown in FIG. 3, a guide chamber 40 is formed inside of the nozzle 4. The guide chamber 40 includes a three stepped expanding sub-chamber 41, 42, 43. Tapered surfaces 54, 55 are formed between two adjacent stepped expanding sub-chambers, respectively. A tapered surface 44 between a first expanding sub-chamber 41 and a second expanding sub-chamber 42 is formed with a plurality of first flow guide slots 441 which are spaced with an equal distance. A probe 5 is disposed inside the guide chamber 40, as shown FIG. 4.

The probe 5 is formed with three stepped sections 51, 52, 53. Tapered surfaces 54, 55 are formed between two adjacent sections. A tapered surface 55 between a second section 52 and a third section of the probe 5 is formed with a plurality of second guide slots 551 which are spaced with an equal distance.

Figure 5:
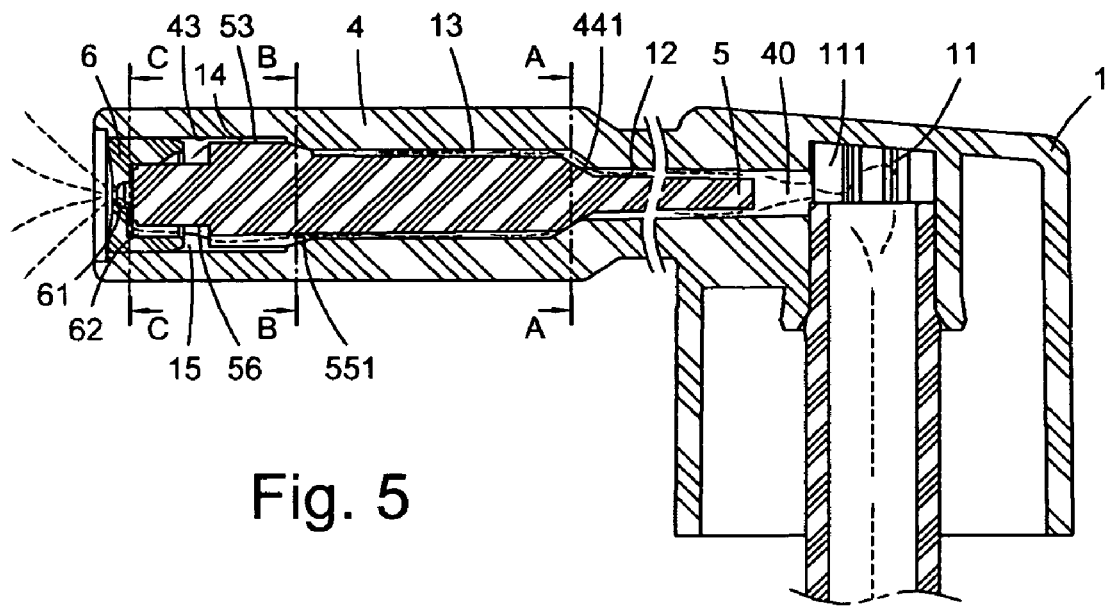
FIG. 5 is another a cross sectional view cross sectional view of the button to show three boosting channels formed between the guide chamber and the probe.

Referring to FIG. 5, after the probe 5 is inserted in the nozzle 4, a first annular boosting channel 12 is formed between the first section 51 of the probe 5 and the first expanding sub-chamber 41 of the guide chamber 40. Similarly, a second annular boosting channel 13 is formed between the second section 52 and the second a third expanding sub-chamber 42, and a third annular boosting channel 14 is formed between the second section 53 and the second a third expanding sub-chamber 43.

Figure 6:
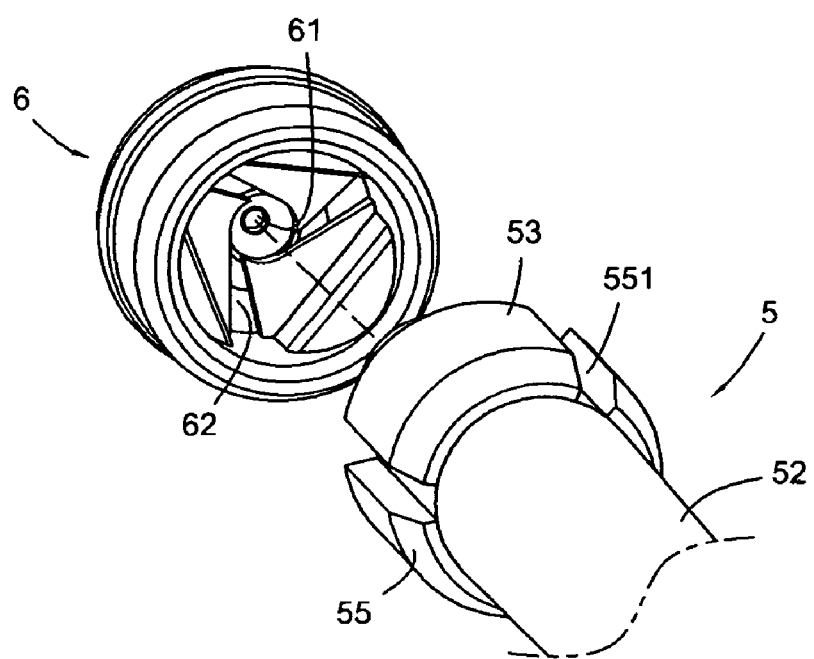
FIG. 6 is a perspective exploded view of the probe and the pressure accumulator with a spraying opening.

A cross-sectional flowing area of the first boosting channel 12 is larger than that of the second boosting channel 13 and similarly the flowing area of the second boosting channel 13 is larger than that of the third booster channel 14. As shown in FIGS. 5 and 6, a distal end of the third section 53 of the probe 5 reduced inwards as a stepped reduced section 56. A pressure accumulator 6 is mounted on the distal end of the probe 5. A pressure accumulating chamber 15 is formed among the pressure accumulator 6, the reduced section 56 and an inner wall of the nozzle 4. A spraying opening 61 is formed on one side of the pressure accumulator 6 facing to the opening of the nozzle 4 so that liquid can be sprayed out therethrough to the external environment. On the other side of the pressure accumulator 6 facing to the pressure accumulating chamber 15, a plurality of slots 62 are formed in a scrolled arrangement on an inner wall thereof.

Referring back to FIG. 1, the dispensing pump 2 has an upper pipe 21 extending to the booster chamber 11 of the button 1 and a lower pipe 22 connecting a tube 23. A closure 24 of the dispensing pump 2 is used to engage with the container 3.

By above components, the pressure of liquid flowing in the nozzle will be increased effectively so that liquid is sprayed out with a higher pressure to increase the spraying speed of the liquid.

When it is desired to spray liquid by pressing on the button I of the atomizer, the booster posts 111 are moved toward the upper pipe 21, the liquid in the booster chamber 11 is pushed into the guide chamber 40.

Figure 7:
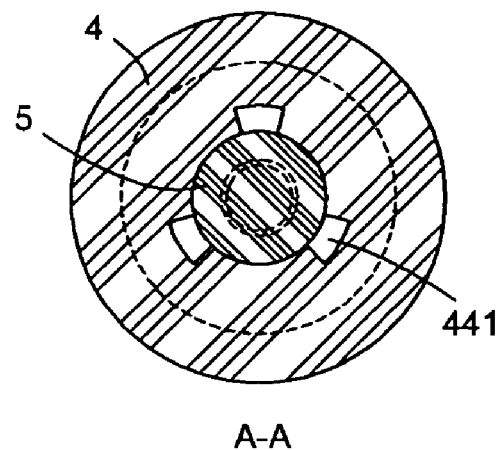
FIG. 7 is a cross section view along line A-A of FIG. 5 to show plural first flow guide slots formed between a first and a second expanding sub-chambers of the guide chamber.
Figure 8:
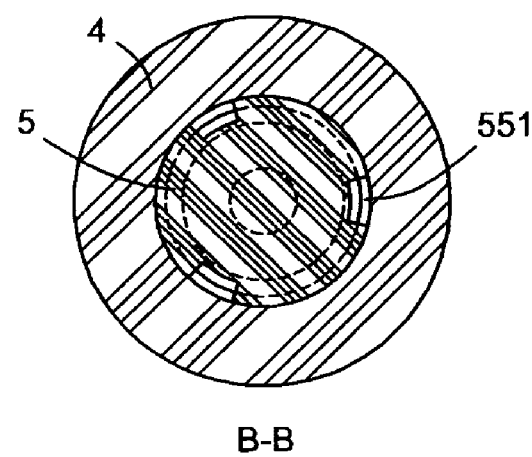
FIG. 8 is a cross section view along line B-B of FIG. 5 to show plural second flow guide slots formed between a second and a third sections of the probe.
Figure 9:
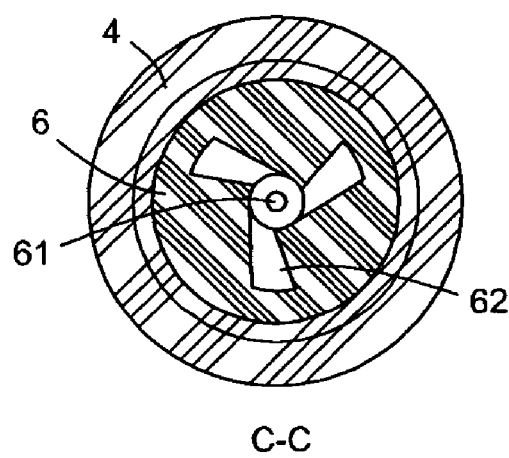
FIG. 9 is a cross section view along line C-C of FIG. 5 to show plural slots formed in a scrolled arrangement on an inner wall of the pressure accumulator.

When liquid flows into the guide chamber 40, the liquid will be hindered by the probe 5 firstly so as to distribute along the periphery of the probe 5. The liquid flows into the second boosting channel 13 and the third boosting channel 14 from the first boosting channel 12 between the guide chamber 40 and the probe 5 so that the speed of the liquid increases. Then the liquid flows through the first flow guide slots 441, and the second flow guide slots 551, as shown in FIGS. 7 and 8, so that the liquid can be guided to the pressure accumulating chamber 15. Finally, the liquid flows through the scrolled slots 62, as shown in FIG. 9, toward the spraying opening 61 and then sprays out with high speed.

Since the speed of the liquid sprayed out increases, the atomized liquid sprayed out will be finer to have an excellent atomization effect so that the spraying effective area is enhanced.

The three stepped expanding sub-chambers 41, 42, 43 of the guide chamber 40 incorporating with three stepped sections 51, 52, 53 of the probe 5 are only examples of the present invention. The number of layers of the guide chamber and the sections of the probe 5 are various. Any telescopic structure or even tubular structure inside the nozzle is acceptable.

The present invention is thus described; it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A pump-dispensing atomizer comprising:
   a container filled with liquid; and
   a dispensing pump including:
      a closure to engage with the container;
      a pressing button with a booster chamber formed inside;
      a nozzle with one end extending from the pressing button, wherein an interior of the nozzle is formed with a guide chamber, the guide chamber has a plurality of expanding sub-chambers, and one end of the guide chamber is connected to the booster chamber;
      a probe formed with a plurality of sections, wherein after the probe is disposed in the guide chamber, a plurality boosting channels are formed between the expanding sub-chambers and the stepped sections, respectively; and
      a pressure accumulator mounted on the other end of the nozzle, formed with a spraying opening which is communicated to outer environment
   wherein a first tapered surface is formed between two adjacent sections and the first tapered surface is formed with a plurality of first flow guide slots.

2. The atomizer as claimed in claim 1, wherein a second tapered surface is formed between two adjacent expanding sub-chambers and the second tapered surface is formed with a plurality of second flow guide slots.

3. The atomizer as claimed in claim 1, wherein the number of the expanding sub-chambers is equal to that of the sections.

4. The atomizer as claimed in claim 1, wherein the sizes of the boosting channels are sequentially enlarged.

5. The atomizer as claimed in claim 1, wherein a pressure accumulating chamber is formed inside a distal end of the nozzle between the probe and the pressure accumulator.

6. The atomizer as claimed in claim 1, wherein the pressure accumulator has a plurality of slots formed in a scrolled arrangement on an inner wall thereof.

* * * * *